United States Patent [19]

Amadei

[11] Patent Number: 4,931,015

[45] Date of Patent: Jun. 5, 1990

[54] MIRROR PARTICULARLY FOR DENTAL CARE WHOSE MOUNTING IS FIXED TO THE HANDLE AND WHOSE GLASS IS REMOVABLE FROM THE MOUNTING WIRE

[76] Inventor: Daniel Amadei, 18 Route de Cagnes sur Mer, 06610 La Gaude, France

[21] Appl. No.: 224,397

[22] Filed: Jul. 26, 1988

[30] Foreign Application Priority Data

Jul. 31, 1987 [FR] France ................... 87 11084

[51] Int. Cl.⁵ ............................................. A61B 1/24
[52] U.S. Cl. ........................................................ 433/30
[58] Field of Search ................................... 433/29, 30

[56] References Cited

U.S. PATENT DOCUMENTS

| | | | |
|---|---|---|---|
| 751,950 | 2/1904 | Sharp | 433/30 |
| 1,504,343 | 8/1924 | Heard . | |
| 2,192,103 | 2/1940 | Preston . | |
| 2,907,110 | 10/1959 | O'Hara . | |
| 3,829,199 | 8/1974 | Brown . | |

FOREIGN PATENT DOCUMENTS 2488122 2/1982 France .

*Primary Examiner*—Robert Peshock
*Attorney, Agent, or Firm*—Young & Thompson

[57] ABSTRACT

A mirror particularly for dental care. The mounting (3) is securely mounted in a non-removable manner to the handle (2) or to an intermediate sleeve interposed between the mounting (3) and the handle (2) and the glass or reflective insert (4) is mounted removably on the mounting (3). The mounting comprises at the level of the inner ring (5) a groove while the edge of the glass (4) comprises a rounded edge. The branches (6, 7) may comprise one or several bends (14, 15), so that all angles are possible relative to the plane of the glass or reflective insert (4) which permits best visibility to the user.

6 Claims, 5 Drawing Sheets

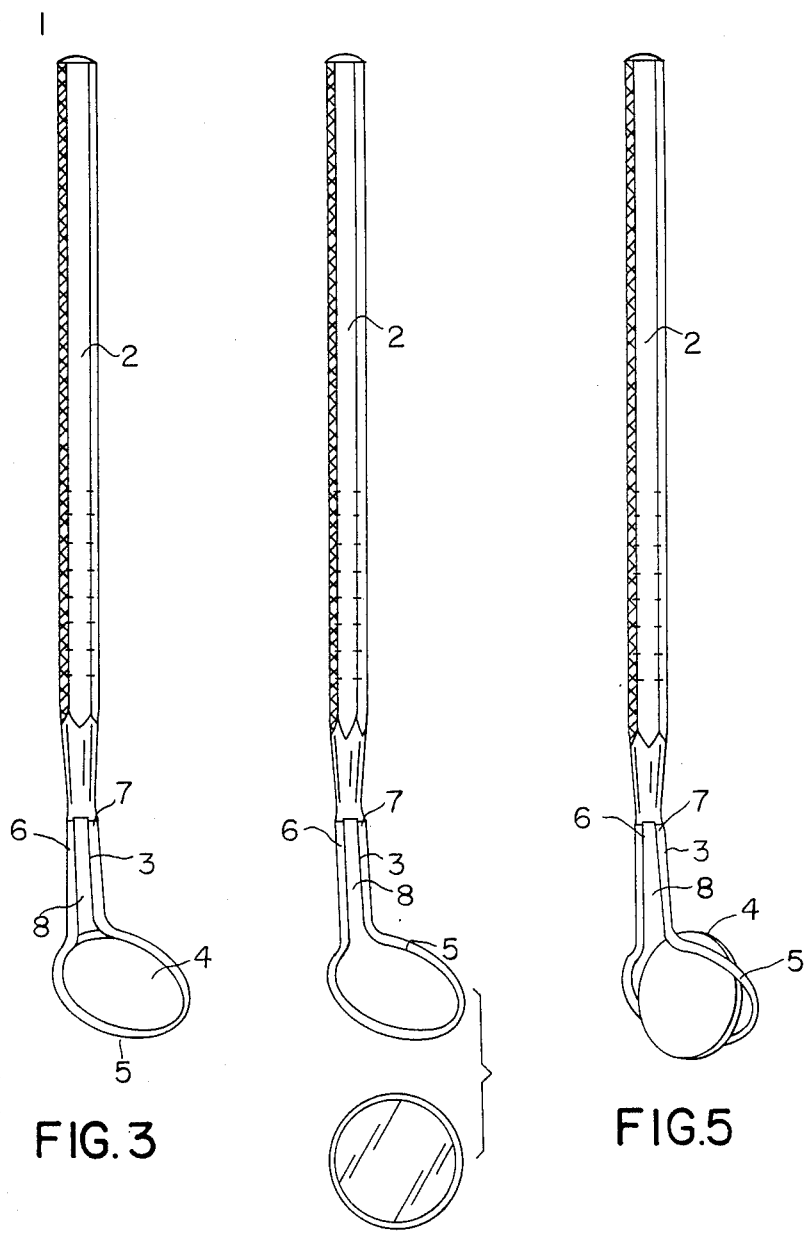

MIRROR PARTICULARLY FOR DENTAL CARE WHOSE MOUNTING IS FIXED TO THE HANDLE AND WHOSE GLASS IS REMOVABLE FROM THE MOUNTING WIRE

The invention has for its object a mirror particularly for dental care whose mounting is secured fixedly by securement means to the handle or to an intermediate sleeve and in which the glass is removable from the mounting wire.

The state of the art may be defined by the following patents:

FR-A-2 448 122—mirror particularly for dental care comprising a glass, a mounting for this glass, and a handle on which the mounting is removably secured.

The mounting 2 of an elastic material comprises: a split ring 4 adapted to receive a glass 1, and two prolonging arms 5 extending from the ring 4 o opposite sides of the slot 6 of this latter; the ring 4 has a portion of smaller cross section 4a situated diametrically oppose the slot 76, an abutment flange 7 projects radially toward the interior from the internal face of the ring 4, and an annular projection 8 protrudes opposite the flange 7.

A principal drawback of this type of dental mirror resides in the fact that the mounting is removably secured to the handle. Said mounting is fixed to the handle by two prolonging arms whose ends are, in general, screw threaded and which, by screwing of the mounting assembly in the recess provided for this purpose, at the end of the handle, permits securement. To change the glass, particularly a normal magnifying glass or insert, of plastic or rhodium and to sterilize the mirror assembly, it is necessary to unscrew the mounting from the handle. This operation is long and delicate. Moreover, the mirror is often used as a separator, and in this case the mounting and its glass turn about the handle as soon as the user exerts pressure, whereupon it is necessary to tighten the screw assembly.

FR-A-2 498 070, FR-A-2 140 871: this dental mirror is constituted as is conventional, by a handle, a mounting and a mirror or reflecting insert mounted in this mounting.

This mounting is constituted by a metal or plastic wire having a certain elasticity adapted to perform in an inclined angle, relative to the axis of the handle, a circular loop which is more or less closed, in which may be mounted and secured a circular reflecting insert whose edge has a groove of a diameter corresponding to that of the wire.

One may thus easily remove the insert, if desired to change and sterilize under ideal conditions all the elements of the mirror.

This dental mirror whose insert or glass is removable has a mounting whose arms serve as the handle. The assembly works if at all only badly, because everything depends on the elasticity of the arms which is variable with time and which varies with the displacement of the pressure point or slide along the handle.

FR-A-2 277 561: describes a dental mirror comprising a handle 11 at an end of which is mounted a mirror 10, and characterized in that an air tube 13 is fixed to this handle and directs an air current on the reflective surface of the mirror, and in that a water tube 12 sends drops of water into the air current proceeding from the tube 13.

All these mirrors require the user to manipulate them to demount them, whereupon the glass often receives fingerprints.

The mirror according to the invention avoids all these drawbacks described above. It permits rapidly changing and under ideal hygienic circumstances, the glass or insert. It permits utilization of a distribution plate which, by using said mirror as a lever, permits ejecting a used glass and replacing another glass in the mounting.

Said mirror is constituted by a handle, a mounting and a reflective insert or glass mounted in this mounting. It is characterized by the fact that the mounting is fixed and immovably mounted to the handle (or an intermediate sleeve between said mounting and the handle) and that the reflective insert or glass is removably mounted on the mounting.

The arms of the mounting or wire are secured to the handle or to its adapter sleeve in a fixed manner for example by deforming the recess and the arms the one in the other or by soldering the arms in their recess. This securement permits the user to use a greater pressure on the mirror while with existing mirrors the mountings and glasses would turn on their screw mounting.

According to another preferred embodiment, the mounting is provided by a wire which forms a split ring adapted to receive the glass and two prolonging arms which extend from said ring on opposite sides of this slot.

The glass and the mounting ring are secured to each other by simple pressure and reception of the edge of one in the groove of the other or vice versa.

According to a preferred embodiment, only one of the faces has a flared edge which permits insertion by simple pressure of one into the other.

According to a preferred embodiment the mounting comprises, at the level of the internal ring, a groove while the edge of the glass comprises a rounded edge.

The face which has a widened edge, to permit the entry or removable by simple pressure, is the rear face. This arrangement permits using the mirror as a spacer and to apply the rear face of the glass and the mounting against a wall, without the glass leaving the mounting.

According to a preferred embodiment, the two ends of the prolongation arms are fixed to the end of the handle while maintaining between them a certain spacing and this in a manner such that the mounting will be more stable and will not turn and that the spacing between the two arms permits the user better to use the mirror as a spacer while maintaining good visibility. The end of the handle opposite the glass may terminate in a conical or truncated conical portion so as to facilitate the reception of a tube for the passage of a fluid through said handle.

According to another embodiment, the handle and/or the sleeve comprises a tube fixed to said handle or an internal conduit of the handle whose outlet opening opens through the end of said handle and/or its sleeve such that the hot air jet or light contacts the forward surface of the glass or reflective insert.

The mounting may comprise longitudinal arms or arms which form several bends, so as to present the glass at an appropriate working angle required by the user. Thus, all the angles are possible with respect to the plane of the glass or insert which permits better visibility by the user.

The sleeve permits receiving all manner of handles by encasement, etc. This sleeve permits the user to chose a handle adapted to his hand and to the work in progress.

Finally, the mirror according to the invention permits changing the glass or reflective insert without touching it. A process of installation of said mirror permits changing the glass or reflective insert.

To this end, the glasses are disposed on a presentation plate on which they are retained by a retention lug.

To eject a glass, it suffices to place the mounting at the level of the split ring and to engage the glass under the retention lug, then it suffices to pull up so as swingingly to disengage upwardly the mirror which frees itself from the glass which remains held by the lug, the glass leaving the edge of the ring by the rear face of the ring of the mounting.

To provide the mirror with another glass or reflecting insert, it suffices to engage an empty mounting at the level of its split ring just above the selected glass, then by a lever motion swinging the mirror and imposing a pressure at the level of the ring so that the glass enters under pressure within the border of the ring, once in place the mirror is laterally disengaged to remove the glass from the retention lug and the mirror may be utilized with its new glass.

Of course, the procedure may be varied if the entry and exit of the glass are effected not via the rear face of the ring of the mounting but via the forward face.

The sleeve, the mounting or wire may be metallic, plastic or any other analogous material corresponding to prevailing practice.

The accompanying drawings are given by way of illustrative non-limiting example. They show a preferred embodiment of the invention. They will permit easy comprehension of the invention.

FIG. 1 is a view of an existing mirror whose mounting is comprised by a shaft of which one end is screw threaded and clamped in the handle and whose other end is soldered to the bowl. The glass is inserted in the bowl. In addition to the drawbacks recited above, it is to be noted that the solder may break.

FIG. 2 is a view of a mirror in which the mounting is a wire which forms an open ring and whose slot is prolonged by two screw-threaded branches. These two screw-threaded branches come together at a securement point. To change the glass or reflective insert, it is necessary to unscrew the mounting. The glass is maintained in its bowl by the gripping of the two branches which are screwed into the handle.

FIGS. 3, 4 and 5 are views of a mirror according to the invention showing the removable nature of the glass as well as the mounting by which the wire is fixed to the handle.

FIG. 3 shows the glass in the mounting.

FIG. 4 shows the glass out of the mounting.

FIG. 5 shows the glass halfway into or leaving the mounting.

Figure 1:
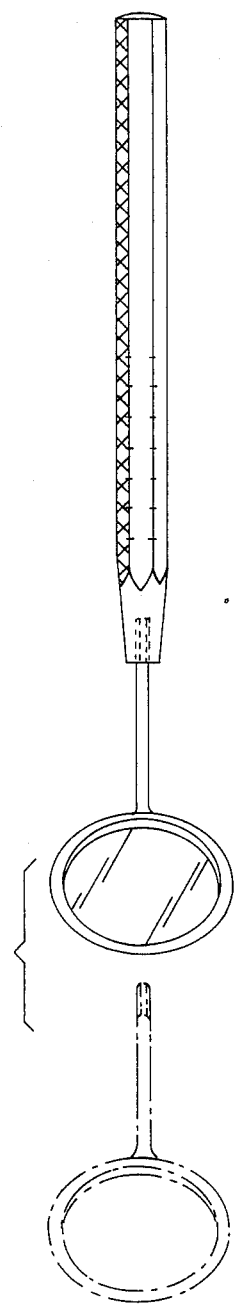
Figure 2:
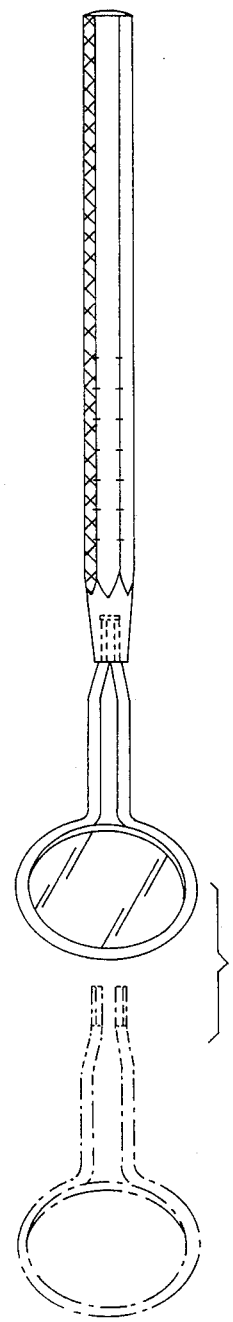
Figure 6:
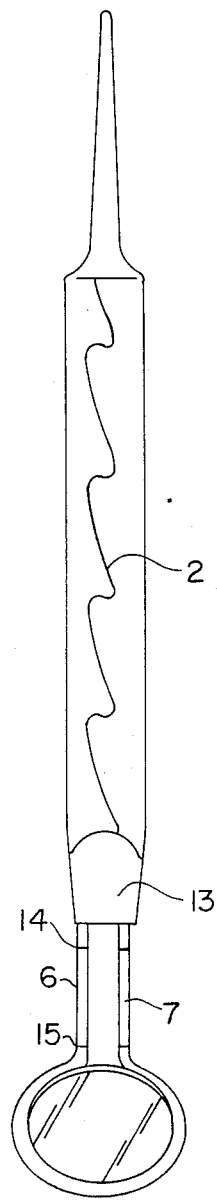
FIG. 6 is an outside view of the mirror according to the invention in which the handle is larger for a better grip and whose end permits connection with a tube.
Figure 7:
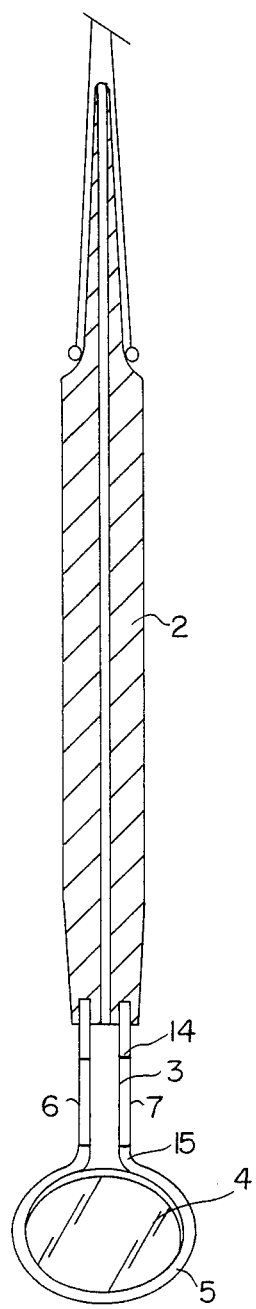
FIG. 7 is a cross sectional view of the mirror of FIG. 6 on its longitudinal axis, so as to show the internal conduit of the handle to convey fluid and/or light onto the forward face of the glass or reflective insert.
Figure 8:
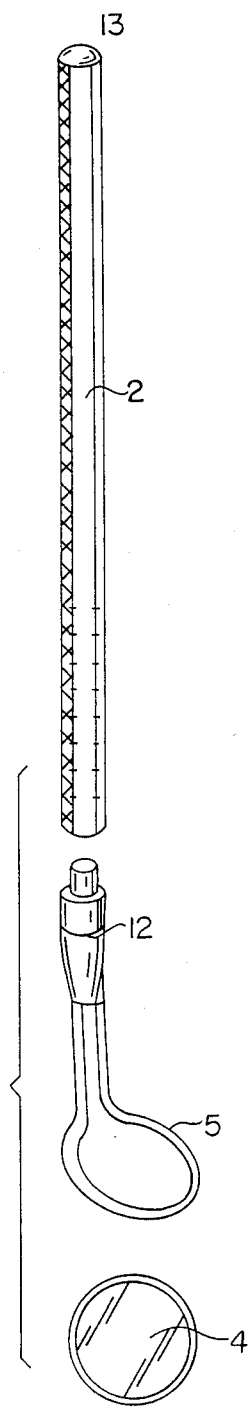
FIG. 8 is an exploded view of the mirror provided with a sleeve disposed between the handle and the mounting.

The mirror is constituted by a handle 2, a mounting 3 or wire 3 and a glass or reflective insert 4.

According to the invention, the mounting 3 is secured to the handle 2 while the glass or reflective insert 4 is removably mounted, see FIGS. 4 and 5.

The mounting 3 is in the form of a wire which forms a split ring 5, adapted to receive the glass 4 and by two prolonging arms 6, 7 which extend from said ring 5 on opposite sides of the slot 8.

The glass 4 and the split ring 5 of the mounting 3 are secured in each other by simple pressure and reception of the edge of one in the groove of the other or vice versa (3, 4 or 4, 3).

Figures 10, 11:
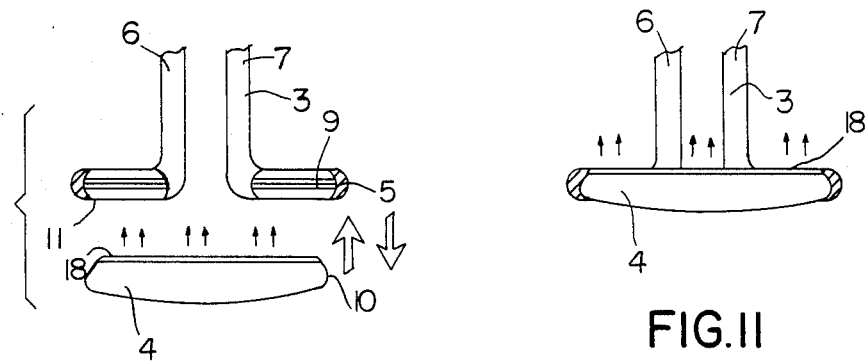
FIG. 10 is a detail view of the ring of the mounting and of the insertion by pressure of the glass in the groove of said mounting.
FIG. 11 is a view similar to FIG. 10 in which the glass has been forcibly inserted into the groove of the mounting of the ring.

In FIGS. 10 and 11, the mounting 3 comprises, at the level of the split ring 5, a groove 9 while the edge of the glass 4 comprises a rounded edge 10 which corresponds to the groove 9.

According to a preferred embodiment, the rear face of the mounting 3 comprises, at the level of the split ring 5, a groove 9 which widens toward the outer wall 11 or outer edge so as to facilitate entry or exit of the glass 4 by this face.

Figure 12:
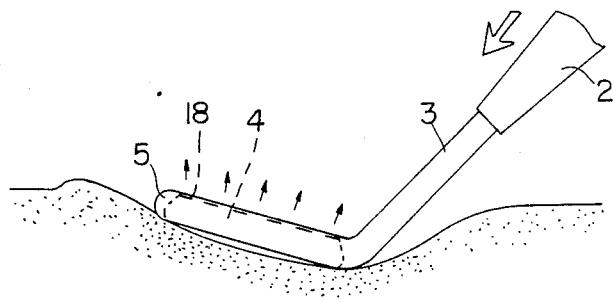
FIG. 12 is a detail view of the mounting seen from the side in which the mirror is used as a spacer against a wall.
Figure 13:
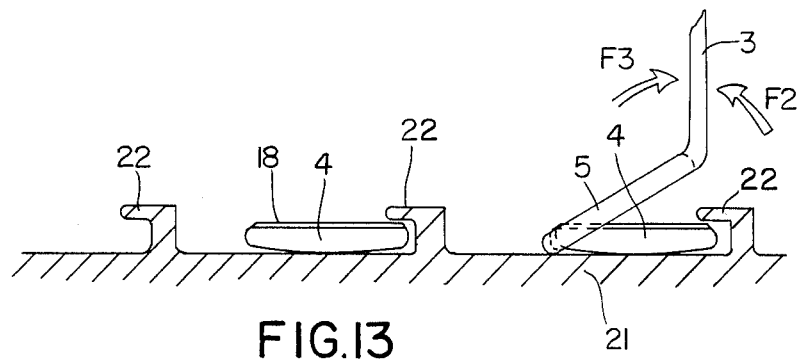
FIG. 13 is a cross sectional view of a presentation slab showing the method of using the mirror to change the glass.

Under these circumstances, as shown in FIG. 12, it is possible to exert a pressure in the direction F1 at the level of the handle 2 without the glass or reflecting insert leaving the ring 5 of the mounting 3.

The branches 6, 7 of the mounting or wire 3 are secured to the handle 2 or to its sleeve 12, for example by compressive deformation at 13 of the recess for the branches 6, 7 located at the end of the handle 2.

The branches 6, 7 may comprise one or more bends 14, 15, so that all angles are possible relative to the plane of the glass or reflective insert 4 which permits better visibility for the user.

Figure 9:
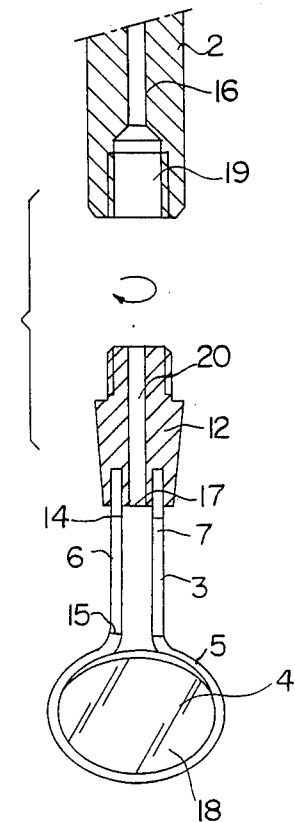
FIG. 9 is a detailed view of said sleeve and of the internal conduit for the projection of a fluid and/or a light.

A mirror 13 may also comprise a sleeve 12 which is interposed between the mounting 3 and the handle 2. The branches 6, 7 of the mounting 3 are fixed to said sleeve 12. Said sleeve 12 may itself be fixed removably o the handle 2. In FIG. 9, the sleeve 12 is screw threaded and is screwed into the recess 19 provided in the handle 2.

According to another embodiment, the handle 2 and/or the sleeve 12 may comprise an internal conduit 16 in the handle 2 and an internal conduit 20 in prolongation thereof in the sleeve 12.

The outlet 17 of this conduit opens at the level of the slot 8 of the mounting 3 so as the jet of fluid (defogging hot air, cleaning water, light), will strike the center of the reflective face 18 of the glass or insert 4.

The mirror 1 according to the invention, permits changing the glass or reflective insert 4 without touching it. A process for using said mirror 1 permits changing the glass or reflective insert 4.

To this end, the glasses 4 are disposed on a presentation slab 21 on which they are retained by retention lug 22.

To eject a glass 4, it suffices to place the mounting 3 at the level of the split ring and to engage the glass under the retention lug, then it suffices to swing to disengage upwardly the mirror 1, see the arrow F2, which frees the glass 4 which remains held by the lug 21, the glass 4 leaves the edge of the ring 5 by the rear face of the ring 5 of the mounting 3.

To provide the mirror 1 with another glass or reflective insert 4, it suffices to engage the empty mounting 3 at the level of its split ring 5 just above the selected glass 4, then to swing in the direction of arrow F3, so as to exert pressure at the level of the ring 5 so that the glass 4 enters under pressure within the edge of the ring, once in place, the mirror 1 is laterally disengaged to remove the glass 4 from the retention lug 22 and the mirror 1 may be used with its new glass 4.

LIST OF REFERENCES

1. Mirror
2. Handle
3. Mounting or wire
4. Glass or insert
5. Split ring
6, 7. Prolongation arms
8. Slot
9. Groove
10. Rounded edge
11. Outer wall
12. Sleeve
13. Deformed grip
14, 15. Bends
16. Internal conduit of the handle
17. Outlet of the conduit
8. Reflective face of the glass
19. Recess
20. Internal conduit of the sleeve
21. Presentation slab
22. Retention lug

What is claimed is:

1. Mirror for dental care, comprising a handle, a mounting and a glass or reflective insert, said mounting comprising a split ring receiving the glass or reflective insert and two arms extending from said split ring and defining a slot therebetween, wherein said mounting is nonremovably fixed to said handle, and wherein said glass or reflective insert is removably mounted in said mounting, whereby a tool may be received in said slot to pry the glass or reflective insert from said mounting.

2. Mirror according to claim 1, wherein said split ring has an interior groove and said glass or reflective insert has a rounded edge of continuously increasing diameter, whereby said glass or reflective insert may be inserted into said split ring by application pressure.

3. Mirror according to claim 1, wherein said arms of said mounting comprise at least one bent portion.

4. Mirror according to claim 1, wherein said handle comprises a proximate end and a distal end, said distal end comprising a sleeve in which said mounting is nonremovably secured.

5. Mirror according to claim 1, wherein said two arms of said split ring are fixed to said handle so as to maintain said slot therebetween, such that said mounting may not rotate relative to said handle.

6. Process for ejecting and replacing the glass or reflective insert of the mounting of a mirror according to claim 1, comprising sliding said mirror relative to a lug projecting from a presentation slab, such that said lug is disposed in said slot between said two arms of said split ring and overlying said glass or reflective insert; lifting said mirror upwardly by said handle, thereby to remove said handle and mounting while leaving said glass or reflective insert behind on the presentation slab, retained by the lug; lowering said mirror devoid of glass or reflective insert onto a new glass or reflective insert retained on the presentation slab by a further lug, such that the lug is received between the two arms of the split ring in the said slot, and pressing downwardly on said glass or reflective insert with said handle and mounting, thereby to insert said glass or reflective insert in said mounting; and sliding the newly assembled mirror laterally relative to the further lug, to remove the newly assembled mirror from the presentation slab.

* * * * *